United States Patent
Kempe

(10) Patent No.: US 7,488,449 B2
(45) Date of Patent: Feb. 10, 2009

(54) PROBE DEVICE FOR MEASURING ETHANOL CONCENTRATIONS IN AN AQUEOUS SOLUTION

(75) Inventor: Eberhard Kempe, Berlin (DE)

(73) Assignee: Biotechnologie Kempe (GmbH), Berlin (DE)

( * ) Notice: Subject to any disclaimer, the term of this patent is extended or adjusted under 35 U.S.C. 154(b) by 662 days.

(21) Appl. No.: 10/761,924

(22) Filed: Jan. 20, 2004

(65) Prior Publication Data

US 2005/0025669 A1 Feb. 3, 2005

(30) Foreign Application Priority Data

Jan. 20, 2003 (DE) ................. 103 02 220
Jan. 27, 2003 (DE) ............. 203 01 212 U

(51) Int. Cl.
*G01N 21/00* (2006.01)
(52) U.S. Cl. ....................................... 422/58
(58) Field of Classification Search ................ 422/100, 422/101, 51; 435/291; 73/863.3, 61.43, 73/19.12, 53.01; 210/500.36; 216/2
See application file for complete search history.

(56) References Cited

U.S. PATENT DOCUMENTS

| | | | | |
|---|---|---|---|---|
| 4,404,284 A | * | 9/1983 | Heider et al. ............. 435/287.1 |
| 4,821,585 A | * | 4/1989 | Kempe ..................... 73/863.23 |
| 4,869,873 A | * | 9/1989 | Klein et al. ..................... 422/51 |
| 5,331,845 A | * | 7/1994 | Bals et al. .................. 73/61.43 |
| 5,979,219 A | * | 11/1999 | Sellmer-Wilsberg et al. ......................... 73/19.12 |
| 6,463,792 B2 | * | 10/2002 | Kempe ...................... 73/53.01 |
| 6,852,223 B2 | * | 2/2005 | Huang et al. ........... 210/500.36 |
| 7,037,438 B2 | * | 5/2006 | Benzel et al. .................. 216/2 |

FOREIGN PATENT DOCUMENTS

| | | |
|---|---|---|
| DE | 31 26 648 A1 | 1/1983 |
| DE | 31 37 765 A1 | 3/1983 |
| DE | 297 01 652 U1 | 5/1997 |
| DE | 298 16 963 U1 | 1/1999 |

(Continued)

OTHER PUBLICATIONS

Groboillot, Ann, Marie-Noelle Pons and Jean-Marc Engasser, Monitoring of volatiles in alcoholic fermentations on molasses via a gas membrane sensor, 1989, Appl Microbiol Biotechnol, (32): 37-44.*

*Primary Examiner*—Walter D Griffin
*Assistant Examiner*—Christine T Mui
(74) *Attorney, Agent, or Firm*—Mayer & Williams PC; Keum J. Park, Esq.

(57) ABSTRACT

The invention relates to a probe device for measuring the concentration of at least one volatile component in an aqueous solution, in particular for measuring the concentration of ethanol, the device having a probe body with an opening, which is tightly covered by a flat membrane, wherein the membrane is permeable for the volatile component, and a sensor for measuring the concentration of the volatile component, wherein the sensor is located inside the probe body and has a sensitive surface, which is located in a first measuring space, wherein an inner side of the flat membrane is part of a second measuring space, wherein the first measuring space and the second measuring space are connected by a measuring aperture, and wherein the first measuring space is connected to a carrier gas exhaust and the second measuring space is connected to a carrier gas supply.

19 Claims, 5 Drawing Sheets

FOREIGN PATENT DOCUMENTS

| | | |
|---|---|---|
| DE | 198 48 542 C2 | 5/2001 |
| DE | 199 59 271 A1 | 6/2001 |
| EP | 0 054 537 B1 | 2/1986 |
| EP | 0 174 417 B1 | 5/1988 |
| EP | 607 756 A2 | 12/1993 |
| WO | WO 97/08533 | 3/1997 |

* cited by examiner

PROBE DEVICE FOR MEASURING
ETHANOL CONCENTRATIONS IN AN
AQUEOUS SOLUTION

FIELD OF THE INVENTION

The invention relates to a probe device for measuring the concentration of at least one volatile component in an aqueous solution, in particular for measuring ethanol concentrations, comprising a probe body having an opening, which is enclosed by a flat membrane being permeable for the volatile component, and a sensor located inside of the probe body, which sensor is sensitive for the volatile component, wherein the inner side of the flat membrane is part of a measuring space. The invention further relates to process of operating such a probe device. Such probe devices are particularly useful in the fields of process supervision and/or process control of chemical, bio-technological, food processing and pharmaceutical processes. The concentration of one or several highly volatile components in a process solution resting in a batch or flowing through a tube is measured, and the processing of the solution is controlled and/or regulated according to the determined concentrations. This may be performed in an on-line, in-line or off-line mode. In the two first mentioned modes, the probe is immersed into the process solution and concentrations are measured in real time. On-line measurements may be performed either by immersion into the solution within a reactor or a tube, whereas in-line measurements are carried out using a by-pass tube, wherein the probe is immersed into the solution within the by-pass. In the off-line mode a sample is taken from the process solution and tested by immersing the probe into the sample. Volatile components are substances the boiling points of which are typically lower than that of water. Examples for such substances are C1 to C8 hydrocarbons, C1 to C6 alkyl monoalcohols, in particular ethanol, C1 to C6 alkyl aldehydes, C1 to C6 alkyl ketones, C1 to C6 alkyl carboxyl acids, benzole, alkyl-substituted benzole, phenols, oxygen and carbondioxide. The sensor is sealed against the process solution by the flat membrane, and the volatile components of the solution have access to the sensor by permeation through the flat membrane and the opening only. Sensors are for instance commercially available solid state semiconductor detectors and the like. Such a detector typically comprises a semiconductor device, e.g. on the basis of $SnO_x$. Ethanol is reacted at the surface of the semiconductor device and this reaction generates an electrical signal, which is amplified and evaluated in an electronic evaluation unit. The material of the flat membrane is selected according to the volatile component to be measured and such selection is easily made by the skilled artisan. The membranes used for devices according to the invention are also called permeation membranes. Permeation membranes allow permeation of substances in gaseous form only. Fluids, in contrast, cannot permeate such a membrane.

BACKGROUND OF THE INVENTION

A probe of the general construction mentioned above is for instance known in the art from the document DE 297 01 652 U1. This probe operates without a carrier gas. An exchange of the gas within the measuring space with the environment takes place via a defined small exchange opening to the atmosphere in the otherwise enclosed measuring space. Thus, the gas exchange is mainly diffusion controlled. This results in rather long response times for obtaining constant readings, if the concentration of the volatile component in the solution changes, because the time period for achieving the total transport rate equilibrium is determined by the diffusion through the exchange opening and depends on the time for obtaining a steady state equilibrium diffusion rate.

From the documents EP 0 174 417 B1 and DE-199 59 271 A1 a probe device is known, which is useful for measuring on-line, e.g. in-line. The measuring space is sealed against the solution by a permeation membrane formed as a tube, which tightly encloses a probe finger and covers an opening in the probe finger to the measuring space. This probe device is operated using a carrier gas. Probe devices of this general design have proved to work well, but it appears desirable to still reduce response times upon concentration changes of the volatile component in the solution. Further, it appears desirable to provide a probe device which may be made and operated in a more simple manner.

In all probe devices known in the art the response time, in particular the dead time, is at least several seconds and, thus, improvement is needed.

OBJECTS OF THE INVENTION

One object of the invention is to provide a probe for measuring volatile components in an aqueous solution, which may be manufactured at lower costs. A further object of the invention is to provide a probe with very short response times, in particular short dead times, for detecting variations of the concentration of the volatile component in the solution.

SUMMARY OF THE INVENTION

For achieving these objects the invention teaches a probe device for measuring the concentration of at least one volatile component in an aqueous solution, in particular for measuring the concentration of ethanol, comprising: a probe body with an opening, which is tightly covered by a flat membrane, wherein said membrane is permeable for the volatile component, and a sensor for measuring the concentration of the volatile component, wherein said sensor is located inside the probe body and comprises a sensitive surface, which is located in a first measuring space, wherein an inner side of the flat membrane is part of an enclosure of the second measuring space, wherein the first measuring space and the second measuring space are connected by a measuring aperture, and wherein the first measuring space is connected to a carrier gas exhaust and the second measuring space is connected to a carrier gas supply. Suitable sensors comprise in particular the solid state detectors described above in conjunction with appropriate electronic evaluation units. For the purpose of clarification the following must be considered. A solid state detector, e.g. according to the document DE 297 01 652 generally comprises a detector housing, wherein the sensitive element is located and contacted. The inner space of the detector housing is connected to the surrounding space by a detector opening, which usually is covered by a grid or the like. Such a constructive entity is a sensor in the terminology of the invention. Thus, the first and the second measuring spaces are different from the inner space of a detector, as described above. The sensitive surface in the above terminology corresponds to such a detector opening.

The invention provides a probe device of a constructive simplicity comparable with that of the device according to the document DE 297 01 652. However, the response time is greatly reduced by using a carrier gas. Within the invention the provision of two separate measuring spaces, wherein the first measuring space is connected to the second measuring space with regard to carrier gas flow, is of significant importance. Surprisingly, a response time, in particular dead time, is obtained, which is even lower than that of a device according to any of the documents EP 0 174 417 or DE-199 59 271, and which is typically below 1 s, or even below 0.5 s. This is surprising since the known devices are also operated using a carrier gas. The reason for the low response time may be, without being bound by such theory, that the transport path of carrier gas loaded with the volatile component from the flat permeation membrane to the sensor is significantly shorter, if compared with the known carrier gas operated devices. This provides for instant response even though the carrier gas flow may be rather low.

The invention further allows using very sophisticated materials for the membrane since the membrane is formed flat and may be made from a sheet material. It is, in particular, not necessary to make a tube, like necessary for the known carrier gas operated devices. The flat membrane may comprise at least two layers, wherein a first layer is a porous carrier layer and the second layer comprises a material permeable for the volatile component, wherein the first layer and the second layer are attached to each other to build a multi layer structure, and wherein the first layer is the inner side of the flat membrane. The porous carrier layer may comprise porous TEFLON® (polytetrafluoroethylene) and the material permeable for the volatile component may be made from a silicon polymer. The first layer may have a thickness in the range from 0.2 to 3.0 mm, and the second layer may have a thickness in the range from 0.01 to 2.0 mm.

According to the invention, the first and the second measuring space may be comparatively small. The first measuring space may have a volume in the range from 10 to 10,000 mm$^3$ and the second measuring space may have a volume in the range from 10 to 10,000 mm$^3$. The provided volume values do not comprise volumes of carrier gas suppy and/or carrier gas exhaust channels within the probe device. The measuring aperture may have an opening area in the range from 1 to 100 mm$^2$ and a length, measured in directions orthogonal to the opening area, in the range from 0.2 to 10 mm.

In an embodiment of significant importance, the second measuring space consists of a pore space of a porous material, preferably of the pore space of the first layer of the flat membrane. In this embodiment the second measuring space does not comprise an open space, but consists of the pore space within the carrier layer of the flat membrane. This allows to arrange support members on the inner side of the membrane supporting the carrier layer. The measuring aperture is then supplied in the support members. Employment of support members allows to operate the probe device at comparatively high fluid pressures in the aqueous solution, i.e. up to 5 bar and more, without risking rupture, dislocation or deformation of the membrane. In particular the stability against deformation is of advantage if the fluid pressure varies, since this stability provides for stabile transport conditions through the membrane at different pressures.

The invention further teaches a method for operating a probe device of the invention, wherein the flat membrane is contacted with the aqueous solution containing the volatile component, wherein the carrier gas supply is connected to a carrier gas source via means for controlling gas flow rates, wherein a defined gas flow from the carrier gas source throw the carrier gas supply into the second measuring space, from the second measuring space through the measuring aperture into the first measuring space, and from the first measuring space to the carrier gas exhaust is established by operation of the means for controlling gas flow rates, wherein the gas flow rate is adjusted in the range from 5 to 100 ml/min.

BRIEF DESCRIPTION OF THE DRAWINGS

In the following, the invention will be described in more detail by reference to drawings showing two preferred embodiments. It is clear to a person skilled in the art that a plurality of variations thereof will fall within the scope of the invention. There are.

DETAILED DESCRIPTION OF THE INVENTION

Figure 1:
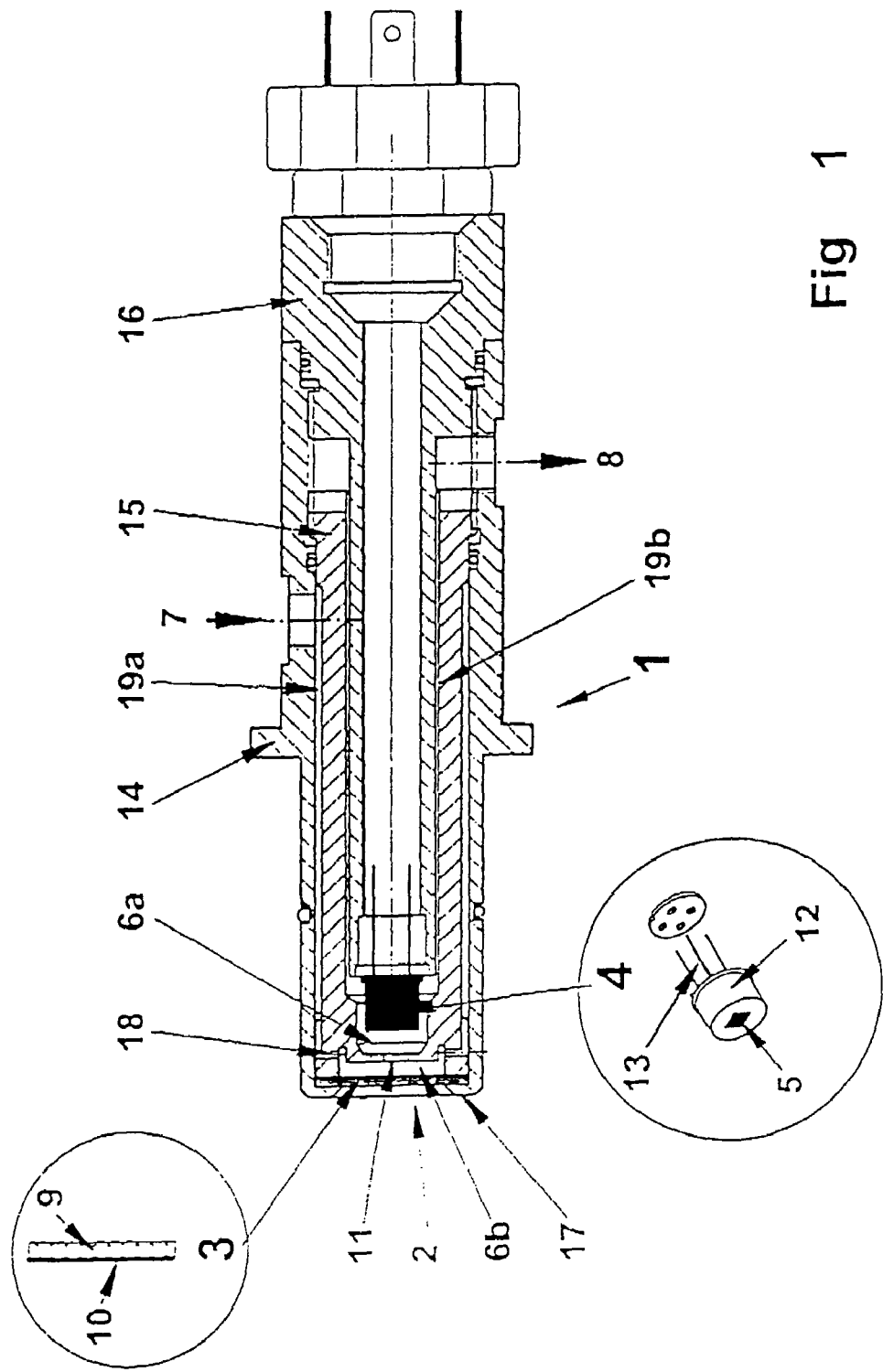
FIG. 1: a probe device according to the invention (cross section)

FIG. 1 shows a probe device for measuring the concentration of ethanol in an aqueous solution, comprising a probe body 1 with an opening 2, wherein the probe body 1 is made essentially of three elements 14, 15, 16. The opening 2 is tightly covered by a flat membrane 3, wherein said membrane 3 is permeable for the volatile component. Within the probe body 1 a sensor 4 for measuring the concentration of the volatile component is arranged. The sensor 4 comprises a commercially available semiconductor solid state detector on SnO$_x$ basis. In the inset showing a detailed view of the sensor 4, it is seen that the sensor 4 further comprises a sensor housing 12 with an opening, which constitutes the measuring area 5 or sensitive surface 5 (both terms are used synonymous) of the sensor 4, and electrical connectors 13, which are contacted to an electronic evaluation unit via connection leads (not shown). The measuring area 5 is located in a first measuring space 6a. The inner side of the flat membrane 3 is part of a second measuring space 6b. The first measuring space 6a and the second measuring space 6b are connected by a measuring aperture 11. The first measuring space 6a is further connected to a carrier gas exhaust 8 and the second measuring space 6b is connected to a carrier gas supply 7. Not shown is that the carrier gas supply 7 is connected to a carrier gas source via means for controlling gas flow rates. In the inset showing a detailed view of the membrane 3, it can be seen that the membrane 3 comprises two layers, wherein a first layer is a porous polytetrafluoroethylene carrier layer 9 and a second layer 10 comprises a silicon polymer material permeable for ethanol, wherein both layers 9, 10 are attached to each other to build a multi layer structure, wherein the carrier layer 9 is at the inner side of the membrane 3.

Figure 3:
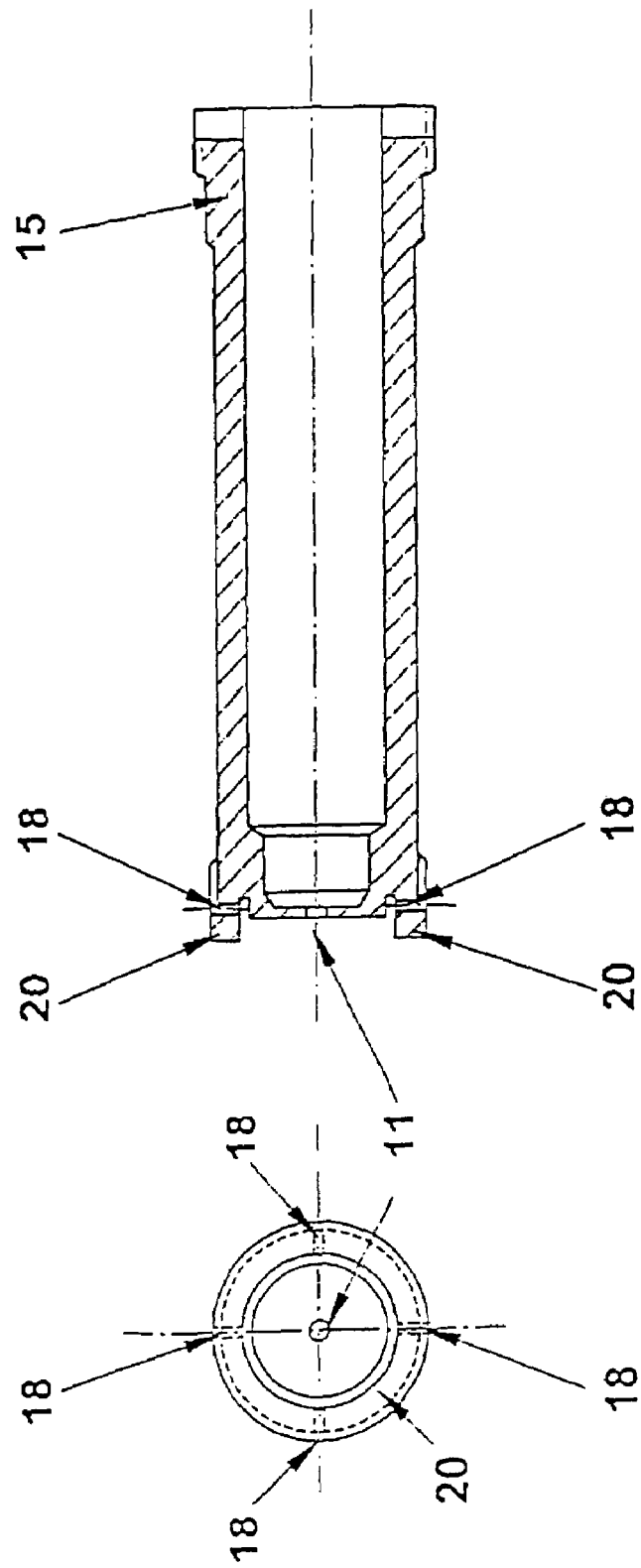
FIG. 3: two different views of a part of the probe device.

The probe body 1 is constructed in detail as following. The probe body 1 consists essentially of three elements 14, 15, 16, which are insertable into each other in a telescopic manner, fixed by screwing into each other, and thereby sealed against each other by at least one seal member. The elements 14, 15, 16 are generally of cylindrical shape and coaxially arranged. The first element 14 constitutes the outer wall of the probe body 1. In a front end thereof the opening 2 is arranged. The second element 15 is inserted into the first element 14. In a front end of the second element 15 the measuring aperture 11 is provided. Further, a ring element 20 is provided at this front end of the second element 15. The inside (shown in FIG. 3) of the preferably cylindrical ring element 20 is part of the inner wall of the second measuring space 6b, wherein the wall thickness of the ring element 20 and the length thereof essentially determine the volume of the second measuring space 6b. The ring element 20 may be an integral part of the second element 15 or be mounted separately. The device is assembled by first positioning the membrane 3 in the first element 14 such that the membrane 3 abuts against the step 17, which is of essentially circular form, and, thus, completely covers the opening 2. Then the second element 15 is inserted and screwed into the first element 14 until the front end of the second element 15 or of the ring element 20 abuts against the membrane 3 and seals the membrane against the first element 14 and the second element 15. Complementary threads for screwing in are provided at the front ends, which are opposite of the membrane 3, of the first element 14 and second element 15. Adjacent seal members are evident from the FIGS. 1 and 4.

The outer diameter of the second element 15 is smaller than the inner diameter of the first element 14 except of the parts, wherein the threads and adjacent seals are positioned. Thereby an annular space 19a is provided between the first element 14 and the second element 15. This annular space 19a is part of the carrier gas supply 7. The carrier gas flows through this carrier gas supply channel 7 to radially orientated channels 18, which are provided adjacent the front end of the second element 15 in the ring element 20 and lead to the second measuring space 6b (the channels 18 may have an axial component). Specific reference is made to FIG. 3, which shows the second element 15 in two different views. As shown, four radial channels 18 are provided.

The third element 16, which comprises the sensor 4, is inserted into the second element 15 in an analogue manner. The third element 16 is, however, not screwed into the second element 15, but into a further complementary thread provided in the first element 14. The first measuring space 6a is provided between the front end of the third element 16 or the sensor 4 and the inner surface of the second element 15. The outer diameter of the third element 16 is smaller than the inner diameter of the second element 15 except of the parts, wherein the threads and adjacent seals are positioned. Thereby a second annular space 19b is provided between the second element 15 and the third element 16. This annular space 19b is part of the carrier gas exhaust channel 8. Thus, the carrier gas flows from the second measuring space 6b through the measuring aperture 11 into the first measuring space 6a comprising the sensor 4 and emits through the second annular space 19b and the carrier gas exhaust 8. From FIG. 1 it is evident, that the first element 14 comprises radial ducts, wherein each one duct communicates with the first annular space 19a or second annular space 19b.

Figure 2:
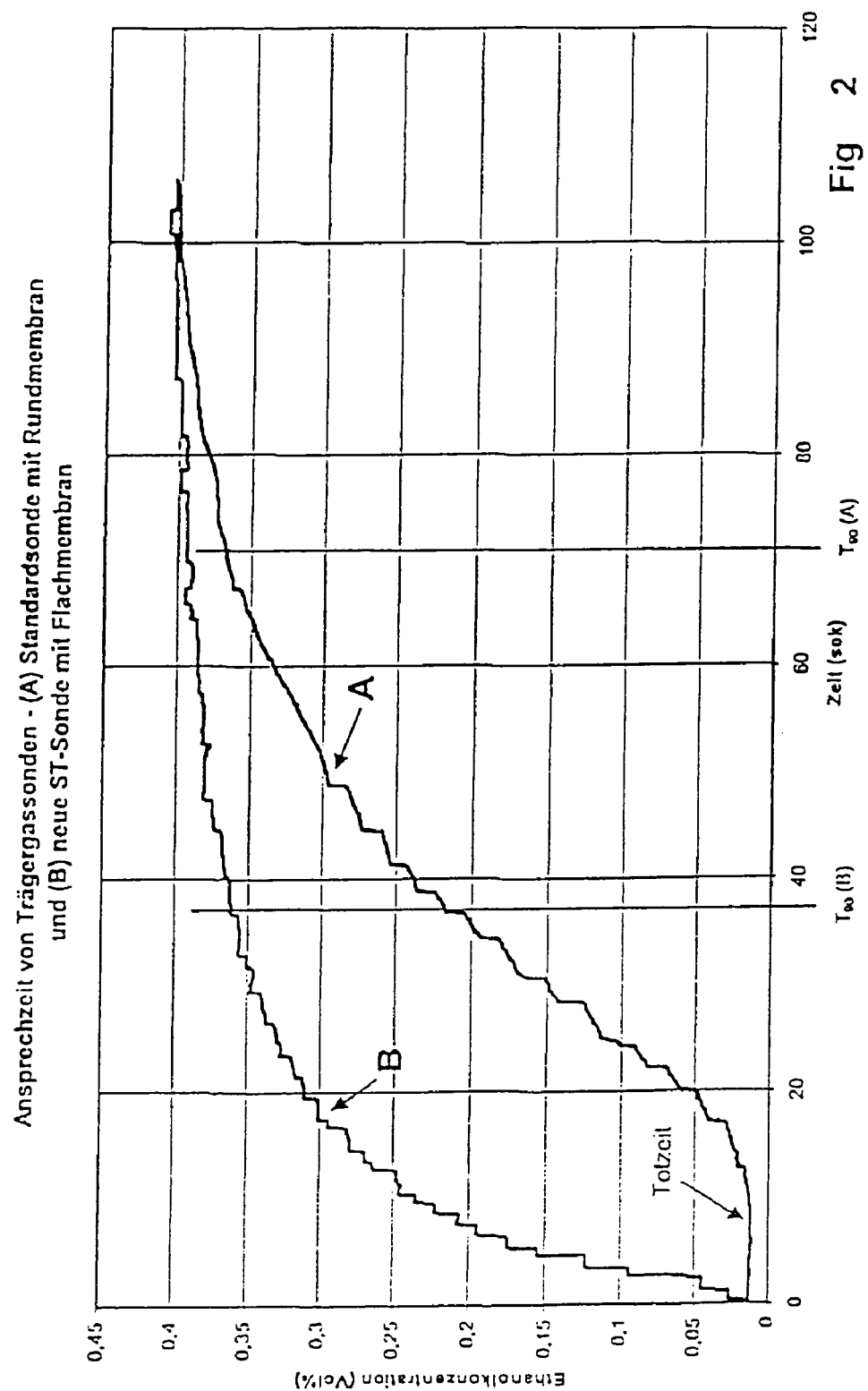
FIG. 2: a diagram showing the response time and dead time measured with a probe device of the invention, compared to the response time and dead time of a carrier gas operated probe device of the art.

FIG. 2 shows different concentration curves dependent on time as obtained for ethanol. The measurements took place with a carrier gas flow rate of 20 ml/min., at 25° C., and an initial concentration step function from 0.0 to 0.4 vol % ethanol in the aqueous solution. Curve A was obtained using a conventional carrier gas probe device as described above. It is evident, that about 72 s lapse until a reading of 90% of the end concentration is obtained. The curve B was obtained with an probe device according to the invention and shows a 90% value of 37 s only. Most important, whereas the state of the art shows at least a dead time of 10 s, the dead time of the invention is in the sub-seconds region, showing practically instant response upon the initial concentration step function. Thus, the probe device of the invention is of particular use for in-line measurements.

Figure 4:
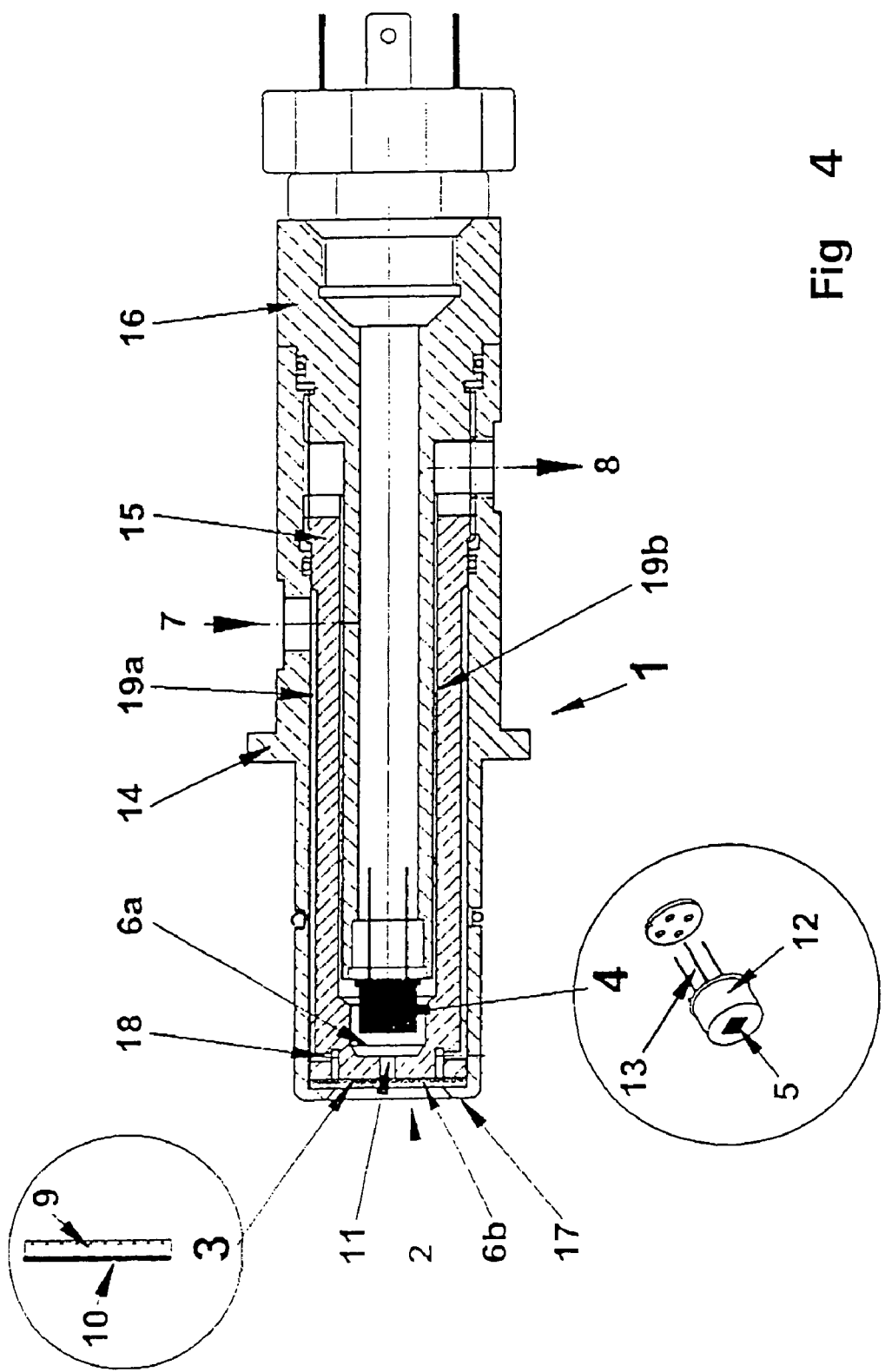
FIG. 4: a variant of the probe device shown in FIG. 1, FIG. 5: the part of FIG. 3, adapted for the probe device according to FIG. 4.
Figure 5:
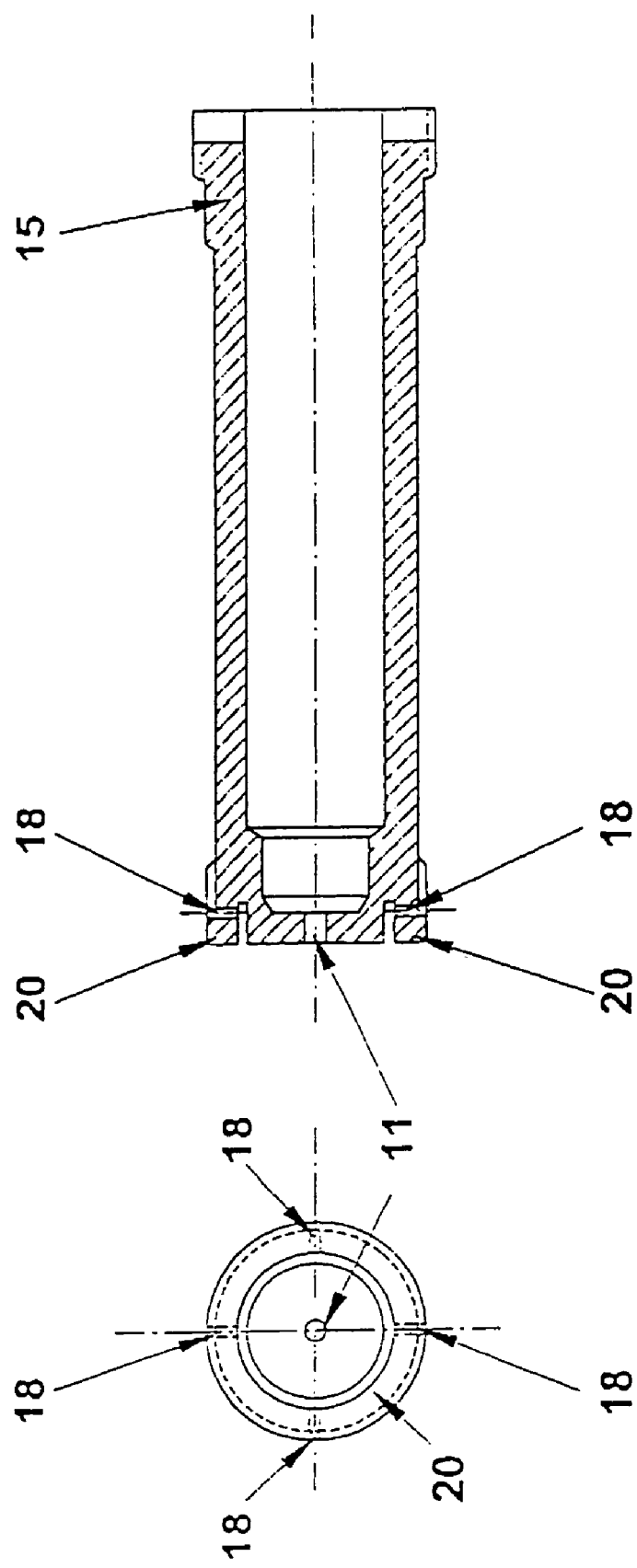

FIG. 4 shows a variant of the probe device of the invention. The above description applies accordingly, except of the following. When comparing the FIGS. 1 and 4, it is evident, that the second measuring space 6b according to FIG. 4 is not an open space, but consists of the open porosity of the carrier layer 9 of the membrane 3. The radial channels 18 end in an annular space (see also FIG. 5). Within this annular space a supporting member for the membrane 3 is provided against which the membrane 3 is supported. The measuring aperture 11 is located in the supporting member. The carrier gas flows through the radial channels 18 into the annular space and further into the pores of the carrier layer 9. Within the carrier layer 9 the carrier gas flows essentially in radial directions and then through the measuring aperture 11 into the first measuring space 6a.

The invention claimed is:

1. A probe device for measuring the concentration of at least one volatile component in an aqueous solution, in particular for measuring the concentration of ethanol, comprising:
   a probe body with an opening, which is tightly covered by a flat membrane, wherein said membrane is permeable for the volatile component, and
   a sensor for measuring the concentration of the volatile component, wherein said sensor is located inside said probe body and comprises a sensitive surface, which is located in a first measuring space,
   wherein an inner side of the flat membrane is part of a second measuring space,
   wherein the first measuring space and the second measuring space are connected by a measuring aperture, and
   wherein the first measuring space is connected to a carrier gas exhaust and the second measuring space is connected to a carrier gas supply.

2. The probe device according to claim 1, wherein the flat membrane comprises at least two layers, wherein the first layer is a porous carrier layer and the second layer comprises a material permeable for the volatile component, and
   wherein the first layer and the second layer are attached to each other to form a multi layer structure, wherein the first layer is the inner side of the flat membrane.

3. The probe device according to claim 2, wherein the porous carrier layer comprises porous polytetrafluoroethylene and the material permeable for the volatile component is a silicon polymer.

4. The probe device according to claim 2, wherein the first layer has a thickness in the range from 0.2 to 3.0 mm, and wherein the second layer has a thickness in the range from 0.01 to 2.0 mm.

5. The probe device according to claim 1, wherein the first measuring space has a volume in the range from 10 to 10,000 mm$^3$ and the second measuring space has a volume in the range from 10 to 10,000 mm$^3$.

6. The probe device according to claim 1, wherein the measuring aperture has an opening area in the range from 1 to 100 mm$^3$ and a length, measured in directions orthogonal to the opening area, in the range from 0.2 to 10 mm.

7. The probe device according to claim 1, wherein the second measuring space consists of a pore space of a porous material.

8. A method for operating a probe device according to claim 1, wherein the flat membrane is contacted with the aqueous solution containing the volatile component, wherein the carrier gas supply is connected to a carrier gas source via means for controlling gas flow rates, wherein a defined gas flow from the carrier gas source through the carrier gas supply into the second measuring space, from the second measuring space through the measuring aperture into the first measuring space, and from the first measuring space to the carrier gas exhaust, is established by operation of the means for controlling gas flow rates, and wherein the gas flow rate is adjusted in the range from 5 to 100 ml/min.

9. The probe device according to claim 1, wherein the probe body comprises three elements, a first element, a second element and a third element, each of the three elements coaxially arranged.

10. The probe device, according to claim 9, wherein the three probe body elements are insertable into each other and are sealed against each other by at least one seal member.

11. The probe device according to claim 9, wherein the three probe body elements are cylindrical.

12. The probe device according to claim 9, wherein a ring element is located at a front end of the second element.

13. The probe device according to claim 12, wherein the inside of the ring element is part of an inner wall of the second measuring space.

14. The probe device according to claim 12, wherein the ring element is an integral part of the second element.

15. The probe device according to claim 12, wherein the ring clement is mounted to the second element.

16. The probe device according to claim 12, wherein the ring element includes a plurality of radially oriented channels.

17. The probe device according to claim 16, wherein each of the plurality of channels lead to the second measuring space.

18. The probe device according to claim 17, wherein there arc four channels.

19. The probe device according to claim 7, wherein the porous material comprises a first layer of the flat membrane.

* * * * *